United States Patent
Halazonetis et al.

(10) Patent No.: US 6,169,073 B1
(45) Date of Patent: Jan. 2, 2001

(54) PEPTIDES AND PEPTIDOMIMETICS WITH STRUCTURAL SIMILARITY TO HUMAN P53 THAT ACTIVATE P53 FUNCTION

(75) Inventors: Thanos Halazonetis, Philadelphia, PA (US); Wolfgang Hartwig, Stamford, CT (US)

(73) Assignees: Bayer Corporation, Westhaven, CT (US); The Wistar Institute, Philadelphia, PA (US)

(*) Notice: Under 35 U.S.C. 154(b), the term of this patent shall be extended for 0 days.

(21) Appl. No.: 08/392,542

(22) Filed: Feb. 16, 1995

(51) Int. Cl.$^7$ .................................................. A61K 38/00

(52) U.S. Cl. ........................... 514/12; 530/300; 530/317; 530/324; 530/323

(58) Field of Search ................................ 435/6, 7.1, 7.23; 514/2, 9, 12; 530/300, 317, 323, 332

(56) References Cited

FOREIGN PATENT DOCUMENTS

| | | |
|---|---|---|
| 518650 | 12/1992 | (EP) . |
| 94/08241 * | 4/1994 | (WO) . |
| WO 94/08241 | 4/1994 | (WO) . |
| 94/10306 * | 5/1994 | (WO) . |
| WO 94/12202 * | 6/1994 | (WO) . |
| WO 95/17213 | 6/1995 | (WO) . |

OTHER PUBLICATIONS

Coller et al., "Substituting Isoserine for Serine in the Thrombin Receptor Activation Peptide SFLLRN Confers Resistance to Aminopeptidase M–induced Cleavage and Inactivation," *J. Biol. Chem.*, 268(28):20741–20743 (1993).

Couder, et al., "Synthesis and Biological Activities of ψ(CH$_2$NH) Pseudopeptide Analogues of the C–terminal Hexapeptide of Neurotensin," *Internat. J. Peptide & Protein Res.*, 41(2):181–183 (1993).

DalPozzo, et al. "H–Gly–Hisψ(NHCO)Lys–OH, Partially Modified Retro–Inverso Analogue of the Growth Factor Glycyl–L–histidyl–l–lysine with Enhanced Enzymatic Stability," *Int. J. Peptide Protein Res.*, 561–566 (1993).

Hupp, et al., "Regulation of the Cryptic Sequence–Specific DNA–Binding Function of p53 by Protein Kinases," Cold Spring Harbor Symposia on Quantitative Biology, vol. LIX, pp. 195–205 (1994).

Hupp, et al., "Small Peptides Activate the Latent Sequence–Specific DNA Binding Function of p53," *Cell*, 83:237–245 (1995).

Shaw et al., "Rgulation of specific DNA Binding by p53: Evidence for a Role for o–Glycosylation and Charged Residues at the Carboxy–terminus," *Oncogene*, 12:921–930 (1996).

Takenaka, et al., "Regulation of the Sequence–Specific DNA Binding Function of p53 by Protein Kinase C and Protein Phosphatases," *J. Biol. Chem.*, 270(10):5405–5411 (1995).

Tanigaki, et al., "The Peptide Binding Specificity of HLA–B27 Subtypes," *Immunogenetics*, 40:192–198 (1994).

Wade–Evans, et al., "Precise Epitope Mapping of the Murine Transformation–Associated Protein, p53" (1985) *EMBO J.*, 4:699–706.

Finlay, et al., "The p53 Proto–Oncogene Can Act As A Suppressor of Transformation" (1989) *Cell*, 57:1083–1093.

Soussi, et al., "Structural Aspects of the p53 Protein in Relation to Gene Evolution" (1990) *Oncogene*, 5:945–952.

Hupp, et al., "Regulation of the Specific DNA Binding Function of p53" (1992), *Cell*, 71:875–886.

Hruby, Victor J., "Conformational and Topographical Considerations in the Design of Biologically Active Peptides" (1993) *Biopolymers*, 33:1073–1082.

Powell, et al., "Peptide Stability in Drug Development. II. Effect of Single Amino Acid Substitution and Glycosylation on Peptide Reactivity in Human Serum" (1993) *Pharma. Res.*, 10:1268–1273.

Hupp, et al., "Activation of the Cryptic DNA Binding Function of Mutant Forms of p53" (1993) *Nucleic Acids Res.*, 21:3167–3174.

Fujiwara, et al., "A Retroviral Wild–Type p53 Expression Vector Penetrates Human Lung Cancer Spheroids and Inhibits Growth by Inducing Apoptosis" (1993) *Cancer Res.*, 53:4129–4133.

Halazonetis, et al., "Wild–Type p53 Adopts a 'Mutant'–Like Conformation When Bound to DNA" (1993) *EMBO J.*, 12:1021–1028.

Halazonetis, et al., "Conformational Shifts Propagate From the Oligomerization Domain of p53 to Its Tetrameric DNA Finding Domain and Restore DNA Binding to Select p53 Mutants" (1993) *EMBO J.*, 12:5057–5064.

Bugg, et al., "Drugs by Design" (1993) *Sci. Am.*, 269:92–98.

Hupp, et al., "Allosteric Activation of Latent p53 Tetramers" (1994) *Current Biology*, 4:865–875.

Friend, S., "p53: A Glimpse at the Puppet Behind the Shadow Play" (1994) *Science*, 265:334–335.

Cho, et al., "Crystal Structure of a p53 Tumor Suppressor–DNA Complex: Understanding Tumorigenic Mutations" (1994) *Science*, 265:346–355.

Clore, et al., "High–Resolution Structure of the Oligomerization Domain of p53 by Multidimensional NMR" (1994) *Science*, 265:386–391.

Speir, et al., "Potential Role of Human Cytomegalovirus and p53 Interaction in Coronary Restenosis" (1994) *Science*, 265:391–394.

(List continued on next page.)

Primary Examiner—Sheela Huff
(74) Attorney, Agent, or Firm—Banner & Witcoff, Ltd.

(57) ABSTRACT

The present invention provides peptides and peptidomimetics corresponding to part or to the entirety of the region encompassed by residues 360–386 of human p53, said peptides and peptidomimetics characterized by the ability to activate DNA binding of wild-type p53 and of select tumor-derived p53 mutants. Pharmaceutical compositions of the compounds of the invention and methods of using these compositions therapeutically are also provided.

13 Claims, No Drawings

OTHER PUBLICATIONS

Cox, et al., "Xenopus p53 is Biochemically Similar to the Human Tumour Suppressor Protein p53 and is Induced Upon DNA Damage in Somatic Cells" (1994) *Oncogene*, 9:2951–2959.

Brady, et al., "Reflections on a Peptide" (1994) *Nature*, 368:692–693.

Jameson, et al., "A Rationally Designed CD4 Analogue Inhibits Experimental Allergic Encephalomyelitis" (1994) *Nature*, 368:744–746.

Moore, Graham J., "Designing Peptide Mimetics" (1994) *Trends Pharmacol. Sci.*, 15:124–129.

Dean, Phillip M., "Recent Advances in Drug Design Methods: Where Will They Lead?" (1994) *BioEssays*, 16:683–687.

Hupp et al, "Small peptides activate the latent sequence-specific DNA binding function of p53" Cell, vol. 83, pp. 237–245.*

Tanigaki et al, "The peptide binding specificity of HLA B27 subtypes", Immunogenetics, vol. 40, pp. 192–198.*

Hupp et al. "Allosteric activation of latent p53 tetramers", Current Biology, vol. 4, No. 10, pp. 865–875.*

Powell et al, "Peptide stability in drug development. II. effect of single amino acid substitution and glysosylation on peptide reactivity in human serum" Parmaceutical Research, vol. 10, No. 9, pp. 1268–1273.*

Couder et al, "Synthesis and biological activities of (Ch2NH) pseudopeptide analogues of the C–terminal hexapeptide of neurotensin", Int. J. Peptide Protein Res., vol. 41, pp. 181–184.*

Dalpozzo et al, "H–Gly–His(NHCO)Lys–OH, partially modifield retro–inverso analogue of the growth factor glycyl–L–histidyl–L–lysine with enhanced enzymatic stability", Int. J. Peptide Protein Res., vol. 41, pp. 561–566*

Stryer. Biochemistry second edition, pp. 13–17.*

* cited by examiner

PEPTIDES AND PEPTIDOMIMETICS WITH STRUCTURAL SIMILARITY TO HUMAN P53 THAT ACTIVATE P53 FUNCTION

FIELD OF THE INVENTION

The present invention relates to the field of peptides derived from tumor suppressor proteins and their use in therapy and drug design.

BACKGROUND OF THE INVENTION

Wild-type (wt) p53 is a sequence-specific DNA binding protein found in humans and other mammals, which has tumor suppressor function [Harris (1993), Science, 262: 1980–1981]. The gene encoding p53 is mutated in more than half of all human tumors, suggesting that inactivation of the function of the p53 protein is critical for tumor development.

The nucleotide sequence of the human p53 gene and the amino acid sequence of the encoded p53 protein have been reported [Zakut-Houri et al. (1985), EMBO J., 4: 1251–1255; GenBank Code Hsp53]. These sequences are presented below as SEQ ID NOs: 1 and 2, respectively. The amino acid sequence of p53 is conserved across evolution [Soussi et al. (1990), Oncogene, 5: 945–952], suggesting that its function is also conserved.

The p53 protein functions to regulate cell proliferation and cell death (also known as apoptosis). It also participates in the response of the cell to DNA damaging agents [Harris (1993), cited above]. These functions require that p53 binds DNA in a sequence-specific manner and subsequently activates transcription [Pietenpol et al. (1994), Proc. Natl. Acad. Sci. USA, 91: 1998–2002]. References herein to DNA binding activity of p53 are concerned with this sequence-specific binding unless otherwise indicated.

In more than half of all human tumors, the gene encoding p53 is mutated [Harris (1993), cited above]. Thus, the encoded mutant p53 protein is unable to bind DNA [Bargonetti et al. (1992), Genes Dev., 6: 1886–1898] and perform its tumor suppressing function. The loss of p53 function is critical for tumor development. Introduction of wild-type p53 into tumor cells leads to arrest of cell proliferation or cell death [Finlay et al. (1989), Cell, 57: 1083–1093; Eliyahu et al. (1989), Proc. Natl. Acad. Sci. USA, 86: 8763–8767; Baker et al. (1990), Science, 249: 912–915; Mercer et al. (1990), Proc. Natl. Acad. Sci. USA, 87: 6166–6170; Diller et al. (1990), Mol. Cell. Biol., 10: 5772–5781; Isaacs et al. (1991), Cancer Res., 51: 47164720; Yonish-Rouach et al. (1993), Mol. Cell. Biol., 13: 1415–1423; Lowe et al. (1993), Cell, 74: 957–967; Fujiwara et al. (1993), Cancer Res., 53: 4129–4133; Fujiwara et al. (1994), Cancer Res., 54: 2287–2291]. Thus, if it were possible to activate DNA binding of tumor-derived p53 mutant proteins, then tumor growth would be arrested. Even for tumors that express wild-type p53, activation of its DNA binding activity might arrest tumor growth by potentiating the function of the endogenous p53 protein.

The N-terminus of p53 (residues 1–90 of the wild-type p53 sequence stored under GenBank Code Hsp53 and repeated here as SEQ ID NO:2; all residue numbers reported herein correspond to this sequence) encodes its transcription activation domain, also known as transactivation domain [Fields et al. (1990), Science, 249: 1046–1049). The sequence-specific DNA binding domain has been mapped to amino acid residues 90–289 of wild-type p53 [Halazonetis and Kandil (1993), EMBO J., 12: 5057–5064; Pavletich et al. (1993), Genes Dev., 7: 2556–2564; Wang et al. (1993), Genes Dev., 7: 2575–2586]. C-terminal to the DNA binding domain, p53 contains a tetramerization domain. This domain maps to residues 322–355 of p53 Wang et al. (1994), Mol. Cell. Biol., 14: 5182–5191]. Through the action of this domain p53 forms homotetramers and maintains its tetrameric stoichiometry even when bound to DNA [Kraiss et al. (1988), J. Virol., 62: 4737–4744; Stenger et al. (1992), Mol. Carcinog., 5: 102–106; Sturzbecher et al. (1992), Oncogene, 7: 1513–1523; Friedman et al. (1993), Proc. Natl. Acad. Sci. USA, 90: 3319–3323; Halazonetis and Kandil (1993), EMBO J., 12: 5057–5064; and Hainaut et al. (1994), Oncogene, 9: 299–303].

On the C-terminal side of the tetramerization domain (i.e., C-terminal to residue 355 of human p53), p53 contains a region that negatively regulates DNA binding. The function of this region is abrogated by deletion of residues 364–393 of human p53 or by deletion of the corresponding residues of mouse p53 (residues 361–390 of the mouse p53 sequence shown in SEQ ID NO: 3) [Hupp et al. (1992), Cell, 71: 875–886; Halazonetis et al. (1993), EMBO J., 12: 1021–1028; Halazonetis and Kandil (1993), cited above].

Thus, deletion of this negative regulatory region activates DNA binding of p53 [Halazonetis and Kandil (1993), cited above; Hupp et al. (1992), cited above]. In addition, incubation of p53 with antibody PAb421, which recognizes p53 at amino acids 373–381, also activates DNA binding, presumably by masking and inactivating this negative regulatory region [Hupp et al. (1992), cited above; Halazonetis et al. (1993), cited above]. We hereinafter refer to this negative regulatory region as NRR1. (We have now developed experimental evidence which suggests that p53 contains additional negative regulatory regions, see Example 3.) Hupp et al. [(1992), cited above] have suggested that NRR1 affects the oligomerization state of wild-type p53 between tetramers and dimers. In contrast, we had proposed that in spite of its proximity to the tetramerization domain, the NRR1 does not affect p53 oligomerization, but rather controls the conformation of p53 [Halazonetis et al. (1993), cited above]. To definitively support our model, we demonstrated that the activated form of p53 that lacks the NRR1 is a tetramer, as is full-length p53 [Halazonetis and Kandil (1993), cited above]. Thus, p53 switches between two conformational states, both tetrameric: an R state with high affinity for DNA and a T state with no or low affinity for DNA [Halazonetis and Kandil (1993), cited above].

Irrespective of the mechanism by which NRR1 controls p53 DNA binding, the potential exists to develop drugs that inactivate this region and upregulate p53 DNA binding. Such drugs would be useful for treatment of cancer, since enhanced p53 function leads to arrest of cell proliferation or to cell death [Finlay et al. (1989), Cell, 57: 1083–1093; Eliyahu et al. (1989), Proc. Natl. Acad. Sci. USA, 86: 8763–8767; Baker et al. (1990), Science, 249: 912–915; Mercer et al. (1990), Proc. Natl. Acad. Sci. USA, 87: 6166–6170; Diller et al. (1990), Mol. Cell. Biol., 10: 5772–5781; Isaacs et al. (1991), Cancer Res., 51: 47164720; Yonish-Rouach et al. (1993), Mol. Cell. Biol., 13: 1415–1423; Lowe et al. (1993), Cell, 74: 957–967; Fujiwara et al. (1993), Cancer Res., 53: 4129–4133; Fujiwara et al. (1994), Cancer Res., 54: 2287–2291].

Lane and Hupp have already suggested that antibody PAb421 can be used for the treatment of cancer, because it activates DNA binding of p53 in vitro (International Patent Application WO 94/12202). However, administration of antibody PAb421 to a patient for this purpose would probably be futile, since antibodies do not readily penetrate cell membranes to reach intracellular proteins, such as p53. Lane and Hupp further argue that any ligand, including small molecule ligands, which bind to the C-terminal 30 amino acids of human p53 would activate its DNA binding activity (International Patent Application WO 94/12202). However, the only ligand they describe (i.e., antibody PAb421) is at least 100 times greater in molecular size than pharmaceutical compounds known to penetrate cells. Their claim further lacks strength, since the C-terminal 30 amino acids of human p53 (residues 364–393 of SEQ ID NO: 2) and the NRR1 do not coincide (although they do overlap).

Thus a need exists to characterize the mechanism by which NRR1 affects DNA binding activity of p53. In particular, a need exists for identification of small molecules which can upregulate p53 binding of DNA. There is a further need for methods which identify tumors expressing p53 mutants whose DNA binding activity can be upregulated by small molecules which have similar effects on wild-type p53. There is also a need for therapeutic methods based on administering such upregulatory molecules to cells which exhibit disease states reflecting low p53 activity.

SUMMARY OF THE INVENTION

It is an object of this invention to provide small molecules which are able to upregulate p53 binding to DNA. Such small molecules can interfere with the function of NRR1, but may not necessarily bind to it.

It is another object of this invention to provide small molecules which upregulate DNA binding by p53 by interfering with the function of the negative regulatory region (NRR1) contained within the p53 C-terminus, preferably to substantially the same extent as monoclonal antibody PAb421.

It is a further object of this invention to provide an assay which identifies the small molecules within the scope of this invention and/or quantitates their activity.

It is yet a further object of this invention to provide a method for identifying those mutant forms of p53 which exhibit DNA binding activity that may be stimulated by the small molecules of this invention.

It is yet another object of this invention to provide a method for stimulating DNA binding activity of p53, or mutant forms of p53, in the cells of patients in need thereof, particularly in tumor cells expressing mutant forms of p53 having DNA binding activity which can be stimulated by the small molecules of this invention.

These and other objects are met by the invention disclosed herein.

The need set forth above for agents that activate DNA binding of human p53 has prompted the present inventors to further study the regulation of human p53. We have mapped NRR1 to residues 361–383 of human p53 (see Example 3). Consistent with our mapping, antibody PAb421, which binds to p53 at i.e., residues 373–381 (within the C-terminal 30 amino acids of human p53) [Wade-Evans and Jenkins (1985), *EMBO J.*, 4:699–706] activates DNA binding [Hupp, et al. (1992), cited above; Halazonetis, et al. (1993), cited above], whereas antibody ICA-9, which binds to p53 residues 382–392 (also within the 30 C-terminal amino acids of human p53) does not activate DNA binding [Hupp and Lane (1994), Current Biology 4: 865–875). These studies have led to the identification of low molecular weight compounds that activate DNA binding of human p53 and are useful in the development of therapies for, and/or the prevention of, cancers, as well as other diseases and disorders caused by inadequate p53 function in vivo. These low molecular weight compounds include peptide fragments and unnatural peptides whose amino acid sequence is derived from NRR1 of p53, modifications of these peptides, and peptidomimetics having the desired activity.

Thus the present invention provides peptides whose amino acid sequence is derived from p53 and peptidomimetics based on the structure of such peptides, as well as methods for the use of these peptides and peptidomimetics in therapy of cancer and other disorders characterized by excessive proliferation of certain cells and tissues. In a preferred mode the peptides of this invention are not sub-fragments of p53, although their amino acid sequence is derived from the linear sequence of human p53 or the corresponding sequences of non-human p53. Particularly, suitable non-human p53 sources include mouse, chicken, xenopus and trout.

In one aspect, the present invention provides peptides which are capable of activating the DNA binding activity of the wild-type p53 tumor suppressor, as well as of mutant forms of p53 associated with certain human tumors. Such peptides include peptides which contain amino acid sequences corresponding to amino acid residues (aa) 363–373, 368–380, 373–383, 371–383, 363–382, 367–386, 363–386, 362–386 and 360–386 of p53.

In another aspect, the present invention provides D-amino acid peptides with sequences corresponding to p53 amino acid residues (aa) 363–373, 368–380, 373–383, 371–383, 363–382, 367–386, 363–386, 362–386 and 360–386, but in the reverse orientation relative to human p53 (reverse-D peptides), which peptides are capable of activating the DNA binding activity of the wild-type p53 tumor suppressor, as well as of mutant forms of p53 associated with certain human tumors.

In a further aspect, the invention provides for modified versions of the peptides described above, including both analogs that contain the peptides described above or analogs and fragments thereof and corresponding sequences of non-human p53 origin. All peptides of this invention share the ability to activate the DNA binding activity of human p53.

In another aspect, the invention provides peptidomimetic compounds, which are non-peptide compounds having the same three-dimensional structure as the peptides of this invention or compounds in which part of a peptide according to this invention is replaced by a non-peptide moiety having the same three-dimensional structure. The invention also provides methods for selecting such peptidomimetic compounds.

Yet another aspect of this invention provides a pharmaceutical composition comprising one or a combination of the above-identified peptides or peptidomimetics in a pharmaceutically acceptable carrier.

Still other aspects of this invention involve methods of using the pharmaceutical compositions of this invention for activating p53 function in human subjects. Such activation would: 1) induce the cellular response to DNA damaging agents, thereby increasing the resistance of healthy subjects to DNA damaging agents, such as sunlight, radiation, etc., and reducing the toxicity of therapies employing DNA damaging agents, such as cancer therapy, 2) induce apoptosis of lymphocytes, thereby conferring immune tolerance for patients with autoimmune diseases, allergies or for transplant recipients, 3) enhance p53 function of abnormally proliferating cells, such as those associated with cancer, psoriasis, etc., thereby leading to treatment by apoptosis or growth arrest of such cells.

Without wishing to be bound by theory, the inventors selected the peptides of this invention from the complete p53 sequence based on their finding that two negative regulatory regions exist in p53, i.e., the sequence from residues 300–321 of human p53 (NRR2) and the previously recognized regulatory region approximately within residues 361–383 of human p53 (NRR1). The inventors hypothesized that these two sequences physically interact with each other or with a third region in p53, shifting p53 into a conformation with low affinity for DNA. When the interactions of these two negative regulatory regions are disrupted (by deletions within one of the two regions or by a suitable antibody), then p53 shifts into a conformation with high affinity for DNA.

By competing with the endogenous p53 negative regulatory region for binding to these regions, small molecules may disrupt the intramolecular regulatory interactions of p53. The inventors designed peptides corresponding to one of these negative regulatory regions, and observed that the peptides of this invention activate DNA binding of human p53.

Other aspects and advantages of the present invention are described further in the following detailed description of the preferred embodiments thereof.

DETAILED DESCRIPTION OF THE INVENTION

According to this invention, peptides are provided that activate the DNA binding activity of the wild-type form of the p53 tumor suppressor, as well as of certain tumor-derived p53 mutants. The mutants which can be so activated are among the most significant for human tumors. Mutants which may be activated by the peptides of this invention include those characterized by a single amino acid residue modification (substitution) at the following locations in the sequence of p53: (a) Ser at residue 239; (b) His at residue 273; (c) Gln at residue 248; (d) Trp at residue 282; and (e) Cys at residue 273. On the other hand, peptides according to this invention do not activate p53 mutants having only substitution of: His at position 175, Trp at position 248, Ser at position 249 and Ile at position 237.

The small molecules of this invention include peptide derivatives which retain the effective sequence of peptides and are effective in a p53 DNA binding assay (as measured, for example, by the assay procedure in Example 2). The present invention provides small molecules that are peptides which contain amino acid sequences from NRR1 of p53, modified forms of the peptides (which retain the activity of the peptides), or peptidomimetics (which retain the essential three-dimensional shape and chemical reactivity, and therefore the biological activity, of the peptides). The small molecules of this invention usually have molecular weight less than 2,000) daltons (Da), preferably less than 1,500 Da, more preferably less than 1,000 Da, most preferably less than 500 Da, and these small molecules activate DNA binding of wild-type p53 at concentrations of 0.2 mM or lower with the same efficacy as peptides made up of p53 residues 363–373, 368–380, 373–383, 371–383, 363–382, 367–386, 363–386, 362–386 or 360–386.

I. Peptides of the Invention

Peptides of this invention contain amino acid sequences corresponding to at least a part of NRR1 of p53 (residues 361–383 of human p53). These peptides include the following:

```
peptide p53p363-373 [SEQ ID NO: 4]

Arg Ala His Ser Ser His Leu Lys Ser Lys Lys peptide p53p368-380 [SEQ ID NO: 5]

His Leu Lys Ser Lys Lys Gly Gln Ser Thr Ser Arg His peptide p53p373-383 [SEQ ID NO: 6]

Lys Gly Gln Ser Thr Ser Arg His Lys Lys Leu peptide p53p371-383 [SEQ ID NO: 7]

Ser Lys Lys Gly Gln Ser Thr Ser Arg His Lys Lys Leu peptide p53p363-382 [SEQ ID NO: 8]

Arg Ala His Ser Ser His Leu Lys Ser Lys Lys Gly Gln Ser Thr Ser Arg His

Lys Lys peptide p53p367-386 [SEQ ID NO:9]

Ser His Leu Lys Ser Lys Lys Gly Gln Ser Thr Ser Arg His Lys Lys Leu Met

Phe Lys peptide p53p363-386 [SEQ ID NO: 10]

Arg Ala His Ser Ser His Leu Lys Ser Lys Lys Gly Gln Ser Thr Ser Arg His

Lys Lys Leu Met Phe Lys peptide p53p362-386 [SEQ ID NO: 11]

Ser Arg Ala His Ser Ser His Leu Lys Ser Lys Lys Gly Gln Ser Thr Ser Arg

His Lys Lys Leu Met Phe Lys
```

-continued peptide p53p360-386 [SEQ ID NO: 12]

Gly Gly Ser Arg Ala His Ser Ser His Leu Lys Ser Lys Lys Gly Gln Ser Thr

Ser Arg His Lys Lys Leu Met Phe Lys peptide p53p363-370 [SEQ ID NO: 14]

Arg Ala His Ser Ser His Leu Lys peptide p53p368-373 [SEQ ID NO: 15]

His Leu Lys Ser Lys Lys peptide p53-368-372 [SEQ ID NO: 16]

His Leu Lys Ser Lys peptide p53p369-373 [SEQ ID NO: 17]

Leu Lys Ser Lys Lys peptide p53p370-375 [SEQ ID NO: 18]

Lys Ser Lys Lys Gly Gln peptide p53p370-374 [SEQ ID NO: 19]

Lys Ser Lys Lys Gly

It will be apparent to one of skill in the art that other smaller fragments of the above peptides may be selected by one of skill in the art and these peptides will possess the same biological activity. As an example, fragments of the peptide p53p360–386 [SEQ ID NO: 12], ranging in length from 26 amino acids to about 5 amino acids, are included within this invention. In general, the peptides of this invention have at least 4 amino acids, preferably at least 5 amino acids, more preferably at least 6 amino acids.

The peptides of this invention also include peptides having sequences of non-human p53 segments corresponding to the NRR1 region. The amino acid sequence of p53 is conserved across species [Soussi et al. (1990), Oncogene, 5: 945–952 incorporated herein by reference], implying that function is also conserved. Indeed, analysis of xenopus and human p53 proteins has revealed no functional differences [Cox et al. (1994), Oncogene, 9: 2951–2959]. Thus, it is possible to substitute human p53 sequences of the peptides of this invention with the homologous non-human p53 sequences. The sequences of human p53 and select non-human p53 proteins have been aligned by Soussi et al. (1990) [cited above]. This alignment can serve to identify regions that are homologous across species. For p53 species that are not listed by Soussi et al. (1990) [cited above], the alignment to the human p53 sequences can be obtained by computer programs commercially available and known in the art, such as the program BESTFIT of the University of Wisconsin GCG package. The entire peptide sequences presented above can be substituted by the corresponding non-human sequences, or alternatively, a fragment of the above peptide sequences can be substituted by the corresponding non-human sequences.

While the peptides described above are effective in activating DNA binding of wild-type p53 in vitro, their effectiveness in vivo might be compromised by the presence of proteases. Serum proteases have quite specific substrate requirements. The substrate must have both L-amino acids and peptide bonds for cleavage. Furthermore, exopeptidases, which represent the most prominent component of the protease activity in serum, usually act on the first peptide bond of the peptide and require a free N-terminus (Power, et al. (1993), *Pharmaceutical Res.*, 10:1268–1273). Based on these considerations, it is advantageous to utilize modified versions of the peptides described above. The modified peptides retain the structural characteristics of the original L-amino acid peptides that confer biological activity with regard to p53, but because of the modification, they are not readily susceptible to cleavage by proteases and/or exopeptidases.

As contemplated by this invention, the term "peptide" includes modified forms of the peptide, so long as the modification does not alter the essential sequence and the modified peptide retains the ability to activate p53 binding to specific DNA sequences (i.e., sequence specific DNA binding activity). Such modifications include N-terminal acetylation, glycosylation, biotinylation, etc. Particular modified versions of the L-amino acid peptides corresponding to the amino acid sequence of the p53 NRR1 (residues 361–383 of human p53) are described below and are considered to be peptides according to this invention:

A. Peptides With An N-Terminal D-Amino Acid

The presence of an N-terminal D-amino acid increases the serum stability of a peptide which otherwise contains L-amino acids, because exopeptidases acting on the N-terminal residue cannot utilize a D-amino acid as a substrate (Powell, et al. (1993), cited above). Thus, the amino acid sequences of the peptides with N-terminal D-amino acids are usually identical to the sequences of the L-amino acid peptides described above [e.g., SEQ ID NO: 4–12], except that the N-terminal residue is a D-amino acid.

B. Peptides With A C-Terminal D-Amino Acid

The presence of an C-terminal D-amino acid also stabilizes a peptide, which otherwise contains L-amino acids, because serum exopeptidases acting on the C-terminal residue cannot utilize a D-amino acid as a substrate (Powell, et al. (1993), cited above). Thus, the amino acid sequences of the these peptides are usually identical to the sequences of the L-amino acid peptides described above [e.g., SEQ ED NO: 4–12], except that the C-terminal residue is a D-amino acid.

C. Cyclic Peptides

Cyclic peptides have no free N- or C-termini. Thus, they are not susceptible to proteolysis by exopeptidases, although they are of course susceptible to endopeptidases, which do not cleave at peptide termini. The amino acid sequences of the cyclic peptides may be identical to the sequences of the L-amino acid peptides described above [e.g., SEQ ID NO: 4–12], except that the topology is circular, rather than linear.

D. Peptides With Substitution of Natural

Amino Acids By Unnatural Amino Acids Substitution of unnatural amino acids for natural amino acids in a subsequence of the NRR1 of p53 can also confer resistance to proteolysis. Such a substitution can, for example, confer resistance to proteolysis by exopeptidases acting on the N-terminus. Several of the peptides whose amino acid sequence is derived from the NRR1 of human p53 (residues 361–383 of human p53) have serine as the N-terminal residue (see for example SEQ ID NO: 7, 9, and 11). The serine residue can be substituted by the β-amino acid isoserine. Such substitutions have been described (Coller, et al. (1993), *J. Biol. Chem.*, 268:20741–20743, incorporated herein by reference) and these substitutions do not affect biological activity. Furthermore, the synthesis of peptides with unnatural amino acids is routine and known in the art (see, for example, Coller, et al. (1993), cited above).

E. Peptides With N-Terminal or C-Terminal Chemical Groups

An effective approach to confer resistance to peptidases acting on the N-terminal or C-terminal residues of a peptide is to add chemical groups at the peptide termini, such that the modified peptide is no longer a substrate for the peptidase. One such chemical modification is glycosylation of the peptides at either or both termini. Certain chemical modifications, in particular N-terminal glycosylation, have been shown to increase the stability of peptides in human serum [Powell et al. (1993), Pharma. Res., 10: 1268–1273]. Other chemical modifications which enhance serum stability include, but are not limited to, the addition of an N-terminal alkyl group, consisting of a lower alkyl of from 1 to 20 carbons, such as an acetyl group, and/or the addition of a C-terminal amide or substituted amide group. In particular the present invention includes modified peptides consisting of residues 363–373, 368–380, 373–383, 371–383, 363–382, 367–386, 363–386, 362–386 or 360–386 of human p53 bearing an N-terminal acetyl group and a C-terminal amide group.

F. Peptides With Additional Amino Acids

Also included within this invention are modified peptides which contain within their sequences the peptides described above. These longer peptide sequences, which result from the addition of extra amino acid residues are encompassed in this invention, since they have the same biological activity (i.e., activate DNA binding of p53) as the peptides described above.

One specific example of variants of the peptide corresponding to amino acids residues 360–386 of human p53 includes the addition of an N-terminal cysteine which confers to the peptide the ability to form dimers:

```
peptide p53pc360-386 [SEQ ID NO: 22]

Cys Gly Gly Ser Arg Ala His Ser Ser His Leu Lys Ser Lys Lys Gly Gln Ser

Thr Ser Arg His Lys Lys Leu Met Phe Lys
```

While peptides having a substantial number of additional amino acids are not excluded, it will be recognized that some large polypeptides will assume a configuration that masks the effective sequence, thereby preventing binding to p53. Other polypeptides will still bind, but are so bulky that the complex of p53 with peptides will no longer bind to DNA. These derivatives will not enhance p53 action and are thereby excluded from the invention.

G. Peptides With Deleted Amino Acids

Peptides of this invention have amino acid sequences contained within NRR1 of p53. To the extent that a peptide containing the sequence of a segment of NRR1 has the desired biological activity, it follows that a peptide that contains the sequences of two such segments would also possess the desired biological activity, even if these segments were not contiguous within the p53 NRR1. Such peptides can also be described as having a sequence corresponding to the p53 NRR1 with an internal deletion.

The ability of peptides with internal deletions to activate DNA binding of p53 was first realized by the observation that synthesis of peptide p53pC360–386 [SEQ ID NO: 22] also generated peptides lacking a glycine or phenylalanine, or combinations thereof, such as:

```
peptide p53pc360-386DG [SEQ ID NO: 23]

Cys Gly Ser Arg Ala His Ser Ser His Leu Lys Ser Lys Lys Gly Gln Ser Thr

Ser Arg His Lys Lys Leu Met Phe Lys peptide p53pc360-386DF [SEQ ID NO: 24]

Cys Gly Gly Ser Arg Ala His Ser Ser His Leu Lys Ser Lys Lys Gly Gln Ser
```

```
                            -continued
     Thr Ser Arg His Lys Lys Leu Met Lys peptide p53pc360-386DGF [SEQ ID NO: 25]

Cys Gly Ser Arg Ala His Ser Ser His Leu Lys Ser Lys Lys Gly Gln Ser Thr

Ser Arg His Lys Lys Leu Met Lys
```

The ability of the above peptides to activate DNA binding of p53 has prompted us to design additional peptides with single amino acid deletions or longer deletions.

Modified peptides which contain single amino acid deletions also include:

```
     peptide p53p363-370D366 [SEQ ID NO: 20]

Arg Ala His Ser His Leu Lys peptide p53p368-373D369 [SEQ ID NO: 21]

His Lys Ser Lys Lys peptide p53p370-375D374 [SEQ ID NO: 32]

Lys Ser Lys Lys Gln
```

Modified peptides according to this invention, having longer deletions, include:

```
     peptide p53p363-373D369-371 [SEQ ID NO: 33]

Arg Ala His Ser Ser His Lys Lys peptide p53p368-380D372-378 [SEQ ID NO: 34]

His Leu Lys Ser Arg His
```

H. Reverse D Peptides

In another embodiment of this invention the peptides are reverse-D peptides corresponding to the amino acid sequence of the p53 NRR1 (residues 361–386 of human p53). The term "reverse-D peptide" refers to peptides containing D-amino acids, arranged in a reverse sequence relative to a peptide containing L-amino acids. Thus, the C-terminal residue of an L-amino acid peptide becomes N-terminal for the D-amino acid peptide, and so forth. For example, the sequence of the reverse-D peptide corresponding to peptide p53p363–373 [SEQ ID NO: 4] is:

```
     peptide p53RDp363-373 [SEQ ID NO: 13]Lys Lys Ser Lys Leu
         His Ser Ser His Ala Arg
```

The reverse-D sequences of the peptides with SEQ ID NOS: 5–11 are presented as SEQ ID NOS: 13–21. Reverse-D peptides retain the same tertiary conformation, and therefore the same activity, as the L-amino acid peptides, but are more stable to enzymatic degradation in vitro and in vivo, and thus have greater therapeutic efficacy than the original peptide (Brady and Dodson (1994), Nature, 368: 692–693; Jameson et al. (1994), Nature, 368: 744–746).

The peptides of this invention, including the analogs and other modified variants, may generally be prepared following known techniques. Preferably, synthetic production of the peptide of the invention may be according to the solid phase synthetic method. For example, the solid phase synthesis is well understood and is a common method for preparation of peptides, as are a variety of modifications of that technique [Merrifield (1964), J. Am. Chem. Soc., 85: 2149; Stewart and Young (1984), Solid Phase Peptide Synthesis, Pierce Chemical Company, Rockford, Ill.; Bodansky and Bodanszky (1984), The Practice of Peptide Synthesis, Springer-Verlag, New York; Atherton and Sheppard (1989), Solid Phase Peptide Synthesis: A Practical Approach, IRL Press, New York]. See, also, the specific method described in Example 1 below.

Alternatively, peptides of this invention may be prepared in recombinant systems using polynucleotide sequences encoding the peptides. It is understood that a peptide of this invention may contain more than one of the above described modifications within the same peptide. Also included in this invention are pharmaceutically acceptable salt complexes of the peptides of this invention.

II. Peptidomimetics

A peptide mimetic is a molecule that mimics the biological activity of a peptide but is no longer peptidic in chemical nature. By strict definition, a peptidomimetic is a molecule that no longer contains any peptide bonds (that is, amide bonds between amino acids). However, the term peptide mimetic is sometimes used to describe molecules that are no longer completely peptidic in nature, such as pseudo-peptides, semi-peptides and peptoids. Examples of some peptidomimetics by the broader definition (where part of a peptide is replaced by a structure lacking peptide bonds) are described below. Whether completely or partially non-peptide, peptidomimetics according to this invention provide a spatial arrangement of reactive chemical moieties that closely resembles the three-dimensional arrangement of active groups in the peptide on which the peptidomimetic is based. As a result of this similar active-site geometry, the peptidomimetic has effects on biological systems which are similar to the biological activity of the peptide.

The present invention encompasses peptidomimetic compositions which are analogs that mimic the activity of biologically active peptides according to the invention, i.e., the peptidomimetics are capable of activating the DNA binding activity of p53. The peptidomimetic of this invention are preferably substantially similar in both three-dimensional shape and biological activity to the peptides set forth above. Substantial similarity means that the geometric relationship of groups in the peptide that react with p53 is preserved and at the same time, that the peptidomimetic will stimulate the DNA binding activity of wild-type p53 and one or more of the p53 mutants set forth above, the stimulation being within a factor of two of the stimulation exhibited by at least one of the peptides of this invention.

There are clear advantages for using a mimetic of a given peptide rather than the peptide itself, because peptides commonly exhibit two undesirable properties: (1) poor bioavailability; and (2) short duration of action. Peptide mimetics offer an obvious route around these two major obstacles, since the molecules concerned are small enough to be both orally active and have a long duration of action. There are also considerable cost savings and improved patient compliance associated with peptide mimetics, since they can be administered orally compared with parenteral administration for peptides. Furthermore, peptide mimetics are much cheaper to produce than peptides. Finally, there are problems associated with stability, storage and immunoreactivity for peptides that are not experienced with peptide mimetics.

Thus peptides described above have utility in the development of such small chemical compounds with similar biological activities and therefore with similar therapeutic utilities. The techniques of developing peptidomimetics are conventional. Thus, peptide bonds can be replaced by non-peptide bonds that allow the peptidomimetic to adopt a similar structure, and therefore biological activity, to the original peptide. Further modifications can also be made by replacing chemical groups of the amino acids with other chemical groups of similar structure. The development of peptidomimetics can be aided by determining the tertiary structure of the original peptide, either free or bound to p53, by NMR spectroscopy, crystallography and/or computer-aided molecular modelling. These techniques aid in the development of novel compositions of higher potency and/or greater bioavailability and/or greater stability than the original peptide (Dean (1994), BioEssays, 16: 683–687; Cohen and Shatzmiller (1993), J. Mol. Graph., 11: 166–173; Wiley and Rich (1993), Med. Res. Rev., 13: 327–384; Moore (1994), Trends Pharmacol. Sci., 15: 124–129; Hruby (1993), Biopolymers, 33: 1073–1082; Bugg et al. (1993), Sci. Am., 269: 92–98, all incorporated herein by reference]. Once a potential peptidomimetic compound is identified, it may be synthesized and assayed using the DNA binding assay described herein or an appropriate tumor suppressor assay [see, Finlay et al. (1983), Cell, 57: 1083–1093 and Fujiwara et al. (1993), Cancer Res., 53: 4129–4133, both incorporated herein by reference], to assess its activity.

Thus, through use of the methods described above, the present invention provides compounds exhibiting enhanced therapeutic activity in comparison to the peptides described above. The peptidomimetic compounds obtained by the above methods, having the biological activity of the above named peptides and similar three dimensional structure, are encompassed by this invention. It will be readily apparent to one skilled in the art that a peptidomimetic can be generated from any of the modified peptides described in the previous section or from a peptide bearing more than one of the modifications described from the previous section. It will furthermore be apparent that the peptidomimetics of this invention can be further used for the development of even more potent non-peptidic compounds, in addition to their utility as therapeutic compounds.

Specific examples of peptidomimetics derived from the peptides described in the previous section are presented below. These examples are illustrative and not limiting in terms of the other or additional modifications.

A. Peptides With A Reduced Isostere Pseudopeptide Bond [ψ(CH)$_2$NH)]

Proteases act on peptide bonds. It therefore follows that substitution of peptide bonds by pseudopeptide bonds confers resistance to proteolysis. A number of pseudopeptide bonds have been described that in general do not affect peptide structure and biological activity. The reduced isostere pseudopeptide bond is a suitable pseudopeptide bond that is known to enhance stability to enzymatic cleavage with no or little loss of biological activity (Couder, et al. (1993), Int. J. Peptide Protein Res., 41:181–184, incorporated herein by reference). Thus, the amino acid sequences of these peptides may be identical to the sequences of the L-amino acid peptides described above [e.g., SEQ ID NO: 4–12], except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above).

B. Peptides With A Retro-Inverso Pseudopeptide Bond [ψ(NHCO)]

To confer resistance to proteolysis, peptide bonds may also be substituted by retro-inverso pseudopeptide bonds (Dalpozzo, et al. (1993), Int. J. Peptide Protein Res., 41:561–566, incorporated herein by reference). According to this modification, the amino acid sequences of the peptides may be identical to the sequences of the L-amino acid peptides described above [e.g., SEQ ID NO: 4–12], except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus. The synthesis of peptides with one or more reduced retro-inverso pseudopeptide bonds is known in the art (Dalpozzo, et al. (1993), cited above).

C. Peptoid Derivatives

Peptoid derivatives of peptides represent another form of modified peptides that retain the important structural determinants for biological activity, yet eliminate the peptide bonds, thereby conferring resistance to proteolysis (Simon, et al., 1992, Proc. Natl. Acad. Sci. USA, 89:9367–9371 and incorporated herein by reference). Peptoids are oligomers of N-substituted glycines. A number of N-alkyl groups have been described, each corresponding to the side chain of a natural amino acid (Simon, et al. (1992), cited above and incorporated herein by reference). Thus, the sequence of N-alkyl groups of a peptoid corresponding to peptide p53p363–373 [SEQ ID NO: 4] would be:

Narg Nala Nhhis Nhser Nhser Nhhis Nleu Naeg Nhser Naeg Naeg where the correspondence of N-alkyl groups of the peptoid to the natural amino acids is: Narg→Arg Nala→Ala Nhhis→His Nhser→Ser Naeg→Lys. The designation of the peptoid N-alkyl groups follows Simon, et al. (1992) (cited above).

While the example indicated above replaces every amino acid of the peptide with the corresponding N-substituted glycine, it is obvious that not all of the amino acids have to be replaced. For example the N-terminal residue may be the only one that is replaced, or a few amino acids may be replaced by the corresponding N-substituted glycines.

III. Pharmaceutical Compositions

The ability of the above-described peptides and compositions of this invention to activate the DNA binding activity of p53 and thus activate the cellular functions of p53 described above, enables their use as pharmaceutical compositions in a variety of therapeutic regimens. The present invention therefore includes novel therapeutic pharmaceutical compositions and methods for treating a human or animal with such compositions. As used herein, the term "pharmaceutical" includes veterinary applications of the invention.

To prepare the pharmaceutical compositions of the present invention, at least one peptide (or peptidomimetic), or alternatively, a mixture of peptides (or peptidomimetics) of this invention is combined as the active ingredient in intimate admixture with a pharmaceutical carrier selected and prepared according to conventional pharmaceutical compounding techniques. This carrier may take a wide variety of forms depending on the form of preparation desired for administration, e.g., oral, sublingual, rectal, nasal, or parenteral.

Pharmaceutically acceptable solid or liquid carriers or components which may be added to enhance or stabilize the composition, or to facilitate preparation of the composition include, without limitation, syrup, water, isotonic saline solution, 5% dextrose in water or buffered sodium or ammonium acetate solution, oils, glycerin, alcohols, flavoring agents, preservatives, coloring agents starches, sugars, diluents, granulating agents, lubricants, and binders, among others. The carrier may also include a sustained release material such as glyceryl monostearate or glyceryl distearate, alone or with a wax. The amount of solid carrier varies but, preferably will be between about 20 mg to about 1 g per dosage unit.

Pharmaceutical compositions of the peptides of this invention, or derivatives thereof, may therefore be formulated as solutions of lyophilized powders for parenteral administration. The presently preferred method is that of intravenous administration.

Pharmaceutical compositions of this invention may also include topical formulations incorporated in a suitable base or vehicle, for application at the site of the area for the exertion of local action. Accordingly, such topical compositions include those forms in which the formulation is applied externally by direct contact with the skin surface to be treated. Conventional forms for this purpose include but are not limited to creams, ointments, lotions, gels, pastes, powders and formulations having oleaginous absorption, water-soluble, and emulsion-type bases.

Additionally, the compounds of the present invention may also be administered encapsulated in liposomes. The compositions, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such a diacetylphosphate, stearylamine, or phosphatidic acid, and/or other materials of a hydrophobic nature.

The compositions may be supplemented by active pharmaceutical ingredients, where desired. Optional antibacterial, antiseptic, and antioxidant agents may also be present in the compositions where they will perform their ordinary functions.

Dosage units of such pharmaceutical compositions containing the peptides or peptidomimetic compounds of this invention preferably contain about 1 mg–5 g of the peptide or salt thereof.

As used herein, the terms "suitable amounts" or "therapeutically effective amount" means an amount which is effective to treat the conditions referred to below. A peptide or peptidomimetic of the present invention is generally effective when parenterally administered in amounts above about 1 mg per kg of body weight to about 30 mg/kg.

IV. Methods of Treatment/Utilities

The pharmaceutical compositions described above and identified with the ability to activate the DNA binding activity of p53 are useful in therapeutic regimens which exploit the cellular functions of p53.

As one example, the pharmaceutical compositions of this invention may be employed to induce the cellular response to DNA damaging agents, such as UV irradiation, radiation and chemotherapeutics used for cancer treatment. By administering a suitable amount of a composition of this invention, patients may tolerate higher doses of such DNA damaging agents. For example, pharmaceutical compositions of this invention may take the form of sunscreens or other sun protective compositions which are administered topically. Alternatively, compositions of this invention may be administered parenterally (for example, intravenously) as an adjunct to patients receiving traditional cancer therapy, which employs the use of DNA damaging agents (eg. radiation therapy and chemotherapy). Other modes of administration may be employed where appropriate.

The compositions of this invention may also be employed as the sole treatment for patients with cancer to enhance the tumor suppressor function of p53, whether wild-type or mutant, present in tumor cells. The administration of the composition to a cancer patient thus permits the arrest of the growth or proliferation of tumor cells or apoptosis (cell death) of tumor cells. Desirably, a suitable amount of the composition of this invention is administered systemically, or locally to the site of the tumor.

Additionally, the compositions of this invention may be administered in methods to suppress cell proliferation in diseases other than cancers, which are characterized by aberrant cell proliferation. Among such diseases are included psoriasis, atherosclerosis and arterial restenosis. This method is conducted by administering a suitable amount of the selected composition topically, locally or systemically to a patient.

Another therapeutic use of the compositions of this invention is in inducing apoptosis of specific cells, such as proliferating lymphocytes. According to this method of use, a suitable amount of a composition of this invention is administered to a subject to enhance the development of immune tolerance. This method may employ both in vivo and ex vivo modes of administration. Preferably, this therapy is useful as the sole treatment or as an accessory treatment to prevent transplant rejection or to treat autoimmune diseases, e.g., systemic lupus erythematosis, rheumatoid arthritis and the like.

The peptides and peptidomimetics of the invention may also be utilized in methods for monitoring disease progression, particularly in a patient receiving therapy as provided by the present invention, or to determine which patients are suited for this therapy. Such a method involves obtaining a tumor biopsy from the patient, preparing an extract [Halazonetis et al. (1993), cited above], and testing this extract for p53-dependent DNA binding in the presence and absence of a peptide or peptidomimetic of the invention (e.g., as described in Example 2, below). If the peptide increases DNA binding, then therapeutic use of the compositions of this invention is indicated and outcome of therapy is improved.

EXAMPLES

The following examples illustrate the preferred compositions and methods of this invention. In view of this disclosure, it will be clear to one of skill in the art that other useful fragments and analogs of the peptides described herein are readily identifiable by one of skill in the art, and are therefore encompassed in this invention. These examples are illustrative only and do not limit the scope of the invention.

Example 1

Synthesis of Peptides

Peptides corresponding to the negative regulatory region 1 (NRR1) spanning residues 361–383 of human p53 were synthesized. Peptides were assembled on a Milligen 9050 automated synthesizer using the standard Fmoc-protocol [Fields and Noble (1990), Int. J. Pept. Protein Res., 35: 161–214]. After cleavage, the peptides were purified by reverse phase HPLC using a C18 column and a linear gradient of acetonitrile in 0.1% aqueous trifluoroacetic acid. The efficiency and accuracy of synthesis was monitored by amino acid composition analysis and/or mass spectroscopy. The present invention is not limited by the specific chemistry or synthesizer used to prepare the peptides of this invention; and such factors are not critical for the activities of the peptides of this invention.

The following peptides were synthesized:

```
peptide p53p363-373 [SEQ ID NO: 4]
    Arg Ala His Ser Ser His Leu Lys Ser Lys Lys
peptide p53p368-380 [SEQ ID NO: 5]
    His Leu Lys Ser Lys Lys Gly Gln Ser Thr Ser Arg His
peptide p53p373-383 [SEQ ID NO: 6]
    Lys Gly Gln Ser Thr Ser Arg His Lys Lys Leu
peptide p53p371-383 [SEQ ID NO: 7]
    Ser Lys Lys Gly Gln Ser Thr Ser Arg His Lys Lys Leu
peptide p53p363-382 [SEQ ID NO: 8]
    Arg Ala His Ser Ser His Leu Lys Ser Lys Lys Gly Gln Ser Thr Ser Arg His
    Lys Lys
peptide p53p367-386 [SEQ ID NO:9]
    Ser His Leu Lys Ser Lys Lys Gly Gln Ser Thr Ser Arg His Lys Lys Leu Met
    Phe Lys
peptide p53p363-386 [SEQ ID NO: 10]
    Arg Ala His Ser Ser His Leu Lys Ser Lys Lys Gly Gln Ser Thr Ser Arg His
    Lys Lys Leu Met Phe Lys
peptide p53p362-386 [SEQ ID NO: 11]
    Ser Arg Ala His Ser Ser His Leu Lys Ser Lys Lys Gly Gln Ser Thr Ser Arg
    His Lys Lys Leu Met Phe Lys
peptide p53p360-386 [SEQ ID NO: 12]
    Gly Gly Ser Arg Ala His Ser Ser His Leu Lys Ser Lys Lys Gly Gln Ser Thr
    Ser Arg His Lys Lys Leu Met Phe Lys
peptide p53pc360-386 [SEQ ID NO: 22]
    Cys Gly Gly Ser Arg Ala His Ser Ser His Leu Lys Ser Lys Lys Gly Gln Ser
    Thr Ser Arg His Lys Lys Leu Met Phe Lys
```

All peptides were acetylated at their N-terminus and contained an amide chemical group attached to their C-terminus.

Amino acid composition analysis and mass spectroscopy indicated that peptide p53pC360–386 actually consisted of a mixture of peptides. In addition to the expected peptide, the mixture contained peptides lacking a glycine, a phenylalanine or combinations thereof [SEQ ID NOS: 23, 24 and 25]. Because the latter peptides differ from the expected peptide only at their termini, all these peptides are expected to be biologically active. This is supported by the demonstration below that various peptides corresponding to the central region of p53pC360–386 have biological activity.

Each peptide was dissolved in a conventional buffer, e.g., 10 or 100 mM Tris-Cl buffer pH 8 at a concentration of 10 mg/ml. Any buffer in which the peptides are soluble, and which is compatible with the DNA binding assays described below, may be used. Once dissolved, the peptides were stored at –70° C.

Example 2

DNA Binding Assay

The ability of the peptides of this invention to activate DNA binding of human p53 was assayed using a standard DNA binding assay for p53 [Halazonetis et al. (1993), cited above; Halazonetis and Kandil (1993), cited above]. This assay utilizes in vitro translated human wild-type p53 or tumor-derived p53 mutants and specific oligonucleotides containing p53 binding sites. These reagents and methods for preparing them are described below.

Human p53 was produced by in vitro translation using plasmids containing the full-length p53 coding sequence. Standard cloning procedures [Ausubel et al. (1994), "Current Protocols in Molecular Biology," Greene Publishing Associates and John Wiley & Sons, New York; Inis et al. (1990), PCR Protocols: A Guide to Methods and Applications, Academic Press, San Diego] were used to prepare these plasmids.

Reagents

Plasmid pGEMhump53wt encodes full-length human wild-type p53. This plasmid was prepared by PCR [s et al. (1990), cited above] using a human p53 cDNA, which is readily available to those practicing the art. The PCR procedure was designed to incorporate unique restriction sites within human p53: Kpn I at codon 218, Sst I at codon 299, Sst II at codon 333, Bst BI at codon 338 and Sal I immediately following the termination codon. An Msc I site at codon 138 was eliminated. These changes did not alter the amino acid sequence of the encoded p53, and were only performed to expedite construction of mutant proteins bearing point mutations associated with human cancer. The PCR product of the human p53 cDNA was digested with Nco I and Sal I and cloned in the vector pGEM4 [Promega, Madison, Wis.], which was linearized with Eco RI and Sal I. Synthetic oligonucleotides were used to bridge the Eco RI site of the vector and the Nco I site at the initiation codon of p53. The entire nucleotide sequence of the Eco RI-Sal I human p53 insert in plasmid pGEMhump53wt is presented as SEQ ID NO: 26. Plasmid pGEMhump53wt was used to generate all the p53 mutants described below, as well as for expression of wild-type p53 by in vitro translation.

Plasmid pGEMhump53wt was used to generate plasmids encoding mutant p53 proteins frequently associated with human cancer. The mutations introduced are those that are most frequently associated with human tumors [Caron de Fromentel et al. (1992), Genes Chrom. Cancer, 4: 1–15]. Specifically the following mutants (all single amino acid substitution mutants) were generated: His175, has histidine at position 175 of p53; Gln248, has glutamine at position 248 of p53; Trp248, has tryptophan at position 248 of p53; Ser249, has serine at position 249 of p53; His273, has histidine at position 273 of p53; Cys273, has cysteine at position 273 of p53; Trp282, has tryptophan at position 282 of p53; Ser239, has serine at position 239 of p53; and Ile237, has isoleucine at position 237 of p53. All p53 mutants were generated using PCR [Innis et al. (1990), cited above]. DNA fragments containing the desired mutations were cloned into pGEMhump53wt using the most convenient restriction sites and confirmed by sequencing. The resultant plasmids are named pGEMhump53His175, etc.

Plasmids pGEMhump53D300–308, pGEMhump53D300–317, pGEMhump53D300–321, pGEMhump53D356–393, pGEMhump53D364–393, pGEMhump53D379–393, pGEMhump53D384–393 and pGEMhump53D388–393 encode proteins that contain deletions within human wild-type p53. These deletions involve residues 300–308, 300–317, 300–321, 356–393, 364–393, 379–393, 384–393 and 388–393 of p53 SEQ ID NO: 2, respectively. These deletions were generated using standard recombinant techniques [Ausubel et al. (1994), cited above; Innis et al. (1990), cited above].

Assay Procedure

Plasmids of the pGEMhump53 series were used to produce in vitro transcribed mRNA and subsequently in vitro translated protein, according to standard procedures [Halazonetis et al. (1988), Cell, 55: 917–924]. The in vitro translated proteins were assayed for DNA binding, as previously described [Halazonetis et al. (1993), cited above, and incorporated herein by reference]. Briefly the in vitro translated protein is incubated with a radioactively labeled oligonucleotide containing a p53 binding site in the presence of non-specific competitor DNA. The reaction mixture is incubated 20 min. at room temperature and directly loaded on a native 5% polyacrylamide electrophoresis gel. In this type of DNA binding assay free DNA migrates to the bottom of the gel, whereas p53/DNA complexes migrate more slowly. Thus, the presence of slowly migrating DNA, which can be detected by autoradiography, indicates p53 DNA binding [Halazonetis et al. (1993), cited above; Halazonetis and Kandil (1993), cited above].

As non-specific competitor DNAs we used 0.1 μg single-stranded oligonucleotide MI7 [GAGAGCCCCAGTRACCATAACTACTCT, SEQ ID NO: 27] and 0.05 μg double-stranded oligonucleotide TF3 [ATCACGTGATATCACGTGATATCACGTGAT, SEQ ID NO: 28] per reaction.

A number of double-stranded oligonucleotides containing p53 binding sites were radioactively labeled for these experiments. These included oligonucleotides Ewaf1, BC.V4A and BC. Oligonucleotides BC.V4A and BC contain artificial sites recognized by p53. These three sites are indicated below, and the specific pentanucleotide repeats recognized by p53 are demarcated by hyphens. The sequence of oligonucleotide Ewaf1 (top strand) is: CCC- GAACA-TGTCC-CAACA-TGTTG-GGG [SEQ ID NO: 29]. This oligonucleotide corresponds to the enhancer that drives p53-dependent transcription of the waf1 gene [El-Deiry et al. (1993), Cell, 75: 817–825]. The sequence of oligonucleotide BC.V4A (top strand) is: TC-GAGCA-TGTTC-GAGCA-TGTTC-GAGCATGT [SEQ ID NO: 30], and the sequence of oligonucleotide BC (top strand) is: CC-GGGCA-TGTCC-GGGCA-TGTCC-GGGCATGT [SEQ ID NO: 31]. These DNAs were radioactively labeled using 32P-labeled nucleotides [Halazonetis et al. (1988), cited above].

Results using this assay are presented in Examples 3 through 5, below.

Example 3
Mapping of Negative Regulatory Regions Within Wild-type p53

The p53 DNA binding assay involves incubating in vitro translated p53 with radioactively-labeled DNAs containing p53 binding sites as described in Example 2 above. For these studies, incubation was performed with oligonucleotides BC.V4A. Wild-type p53 binds to this oligonucleotide. However, its DNA binding activity is subject to downregulation by the negative regulatory region 1 (NRR1), which maps to the C-terminus of p53. Thus deletion of residues 364–393 of human p53 activates DNA binding [Hupp et al. (1992), cited above; Halazonetis and Kandil (1993), cited above]. We reproduced this result using oligonucleotide BC.V4A and plasmid pGEMhump53D364–393. However, DNA binding of a deletion mutant lacking residues 353–360 was not activated (see Table 1).

To map more finely the NRR1 and to identify other NRR that might be present in the C-terminus of p53, we examined the DNA binding activities of the p53 deletion mutants described in Example 2 above. As shown in Table 1, mutants p53D356–393, p53D364–393, p53D379–393 were activated for binding to oligonucleotide BC.V4A. In contrast mutants p53D384–393 and p53D388–393 were not. These results map the C-terminal boundary of the NRR1 to residue 383 of p53. The N-terminal boundary of NRR1 is certainly C-terminal to residue 355 of p53, since residues 322–355 of p53 form the p53 tetramerization domain [Wang et al. (1994), cited above]. Analysis of the DNA binding activity of a deletion mutant lacking residues 353–360 indicates that it contains a functional NRR1 (Table 1), which indicates that the N-terminal boundary of NRR1 is at residue 360. Thus, the NRR1 is within residues 361–383 of p53.

Examination of mutants p53D300–308, p53D300–317 and p53D300–321 revealed the unexpected presence of a second negative regulatory region (NRR2), since all these three deletion mutants exhibited activated binding to oligonucleotide BC.V4A. NRR2 does not overlap with the NRR1, since the two NRRs are separated by the p53 tetramerization domain (residues 322–355 of p53 [Wang et al. (1994), cited above]).

TABLE 1

DNA Binding As Measured For Deletion Mutants of p53

| Residues Deleted In Mutant Tested | Binding of Mutant p53 to BC.V4A DNA |
| --- | --- |
| None (wild-type p53) | − |
| 364–393 | 3+ |
| 356–393 | 3+ |
| 379–393 | 3+ |

TABLE 1-continued

DNA Binding As Measured For Deletion Mutants of p53

| Residues Deleted In Mutant Tested | Binding of Mutant p53 to BC.V4A DNA |
| --- | --- |
| 384–393 | +/− |
| 388–393 | +/− |
| 353–360 | +/− |
| 300–308 | 3+ |
| 300–317 | 3+ |
| 300–321 | 3+ |

Example 4
Activation of p53 DNA Binding by Antibody PAb421

The p53 DNA binding assay involves incubating in vitro translated p53 with radioactively-labeled DNAs containing p53 binding sites, such as oligonucleotides BC, BC.V4A and Ewaf1 [see Example 2 above]. The effect on p53 DNA binding of incubation in the presence or absence of 0.1 μg anti-p53 antibody PAb421 (available from Oncogene Science, Uniondale, N.Y.) is shown in Table 2. Wild-type p53 binds to oligonucleotides BC, BC.V4A and Ewaf1, as demonstrated by a slowly migrating 32P-labeled species, which represents the p53/DNA complex. In the presence of antibody PAb421, the slowly migrating 32P-labeled species migrates even more slowly, indicating a greater size, since it now contains antibody PAb421 as well. In addition, in the presence of PAb421, the intensity of the radioactivity emitted by the slowly migrating 32P-labeled species increases, consistent with the observation that antibody PAb421 activates DNA binding of wild-type p53 [Hupp et al. (1992), cited above; Halazonetis et al. (1993), cited above; Halazonetis and Kandil (1993), cited above]. Because wild-type p53 binds quite efficiently to oligonucleotide BC, the ability of antibody PAb421 to activate wild-type p53 DNA binding is more evident with oligonucleotides BC.V4A and Ewaf1. Antibody PAb421 activates DNA binding of wild-type p53 by inactivating the negative regulatory region 1 (NRR1) at the p53 C-terminus (see Background of the Invention).

Some of the p53 mutants frequently associated with human tumors (see Example 2, above) were also examined for DNA binding using oligonucleotide BC (see Table 2). Consistent with previous reports [Bargonetti et al. (1992), cited above], none of them exhibited significant DNA binding activity as compared with wild-type p53. However, in the presence of antibody PAb421 mutants Gln248, His273, Cys273, Trp282 and Ser239 exhibited significant DNA binding activity (see Table 2), which for several of these mutants was equivalent to that of wild-type p53.

TABLE 2

Stimulation of Mutant p53 Binding To BC DNA By Antibody Specific For NRR1

| Amino Acid Substitution In p53 Mutant | Stimulation of DNA Binding By PAb421 |
| --- | --- |
| None | + |
| Gln248 | 2+ |
| His273 | 3+ |
| Cys273 | 3+ |
| Trp282 | 3+ |
| Sep238 | 3+ |

These experiments suggest that inactivation of the NRR1 by PAb421 can restore DNA binding activity to some of the p53 mutants frequently associated with human cancer. The peptides of this invention also inactivate the function of the NRR1 (although by a different mechanism than PAb421), as shown in the following studies. Therefore, the spectrum of p53 mutants that are amenable to therapeutic intervention using the peptides of this invention may be determined by identifying p53 mutants whose DNA binding activity is susceptible to stimulation by PAb421.

Example 5

Activation of p53 DNA Binding by Peptides of the Invention

DNA binding assays were performed as described above (Example 2) in the presence or absence of peptides corresponding to fragments of NRR1 from human p53. The peptides examined are described in Example 1 above and were tested at concentrations ranging between 0.02–0.4 mM. The results are summarized in Table 3.

We first examined the ability of peptide p53pC360–386 to activate binding of wild-type p53 to oligonucleotide BC.V4A. In the absence of the peptide, wild-type p53 binds weakly to this DNA. However, in the presence of 0.02–0.2 mM peptide p53pC360–386, DNA binding of wild-type p53 is activated. The level of activation achieved by 0.02 mM peptide p53pC360–386 is similar to that achieved by 0.1 µg antibody PAb421. The ability of peptide p53pC360–386 to activate DNA binding of wild-type p53 is not limited to oligonucleotide BC.V4A. DNA binding was also activated to oligonucleotide Ewaf1 (see Table 3).

Since peptide p53pC360–386 activated DNA binding of wild-type p53, we subsequently examined whether truncating this peptide at the N- or C-termini would maintain activity. Peptides p53p362–386, p53p363–386, p53p363–382 and p53p367–386 were examined in a DNA binding assay using oligonucleotide Ewaf1, and the data is summarized in Table 3. At peptide concentrations of 0.2–0.3 mM, all peptides activated DNA binding of wild-type p53. An even smaller peptide, p53p371–383, was examined using oligonucleotide BC.V4A. At peptide concentrations of 0.2–0.4 mM, peptide p53p371–383 activated DNA binding of wild-type p53.

We subsequently examined the ability of peptides p53p363–373, p53p368–380 and p53p373–383 to activate DNA binding of wild-type human p53. These peptides correspond to consecutive partially overlapping regions of the p53 NRR1 (residues 363–373, 368–380 and 373–383 of human p53, respectively). All three peptides activated binding of wild-type p53 to oligonucleotide Ewaf1, when tested at a 0.4 mM concentration. Peptides p53p363–373 and p53p368–380 were somewhat more potent than p53p373–383 in activating DNA binding. Nevertheless, these results suggest that peptides corresponding to small regions of the p53 NRR1 can be effective in activating p53 DNA binding. Furthermore, since peptides p53p363–373 and p53p373–383 essentially don't overlap, the stimulatory peptides need not contain a specific minimal fragment of the p53 NRR1.

To examine whether the peptides of this invention also activate DNA binding of p53 mutants, we employed the His273 p53 mutant, as a representative of the class of mutants whose DNA binding can be activated by inactivation of NRR1 (see Example 4 above). The p53His273 mutant fails to bind to oligonucleotide BC using the DNA binding assay described here. However, when incubated with peptides p53pC360–386 or p53p371–383 at 0.2 and 0.4 mM concentrations, respectively, then p53His273 demonstrated DNA binding activity.

We conclude that the peptides of this invention activate DNA binding of wild-type p53 and of select p53 mutants as efficiently as antibody PAb421. While both the peptides of this invention and antibody PAb421 inactivate the NRR1 of p53, their mechanism of action is different. Thus, antibody PAb421 binds to NRR1 and inactivates it by masking it. In contrast, the peptides of this invention compete with the endogenous NRR1 of p53 for binding to a second negative regulatory region, perhaps NRR2. Thus, they are competitors of NRR1, not masking agents.

TABLE 3

Extent of Stimulation by Peptides of p53 Binding to DNA

| Peptide (p53 residues) | Stimulation of wild-type p53 Binding to DNA | |
| --- | --- | --- |
| | BC.V4A | Ewaf1 |
| 360–386 | 3+ | 3+ |
| 362–386 | ND* | 3+ |
| 363–386 | ND | 3+ |
| 363–382 | ND | 3+ |
| 367–386 | ND | 3+ |
| 371–383 | 2+ | ND |
| 363–373 | ND | 3+ |
| 368–380 | ND | 3+ |
| 373–383 | ND | 2+ |
| | Stimulation of DNA Binding by p53 Mutant His273 | |
| 360–386 | 3+ | ND |
| 371–383 | 3+ | ND |

*ND = Not Done

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in medicine, immunology, hybridoma technology, pharmacology, and/or related fields are intended to be within te scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A peptide which competes with an endogenous p53 negative regulatory region for binding with a negative regulatory region of p53, said peptide containing at least four sequential amino acids from a negative regulatory region which maps to residues 361–383 of p53 (SEQ ID NO. 2), said peptide not being a subfragment of human p53, wherein said peptide activates, ia p53 DNA binding assay, DNA binding of wild-type p53 or a p53 mutant containing a single amino acid substitution, said mutant selected from the group consisting of p53-ser$^{239}$, p53-his$^{273}$, p53-gln$^{248}$, p53 trp$^{282}$, and p53 cys$^{273}$, and said peptide containing residues 363–373 (SEQ ID NO.4), 368–380 (SEQ ID NO.5), 373–383 (SEQ ID NO.6), 371–383 (SEQ ID NO.7), 363–382 (SEQ ID NO. 8), 367–386 (SEQ ID NO. 9),363–386 (SEQ ID NO 10), 362–386 (SEQ ID NO.11), 360–386 (SEQ ID NO. 12), 363–370 (SEQ ID NO. 14), 368–373 (SEQ ID NO. 15), 368–372 (SEQ ID NO. 16), 369–373 (SEQ ID NO.17), 370–375 (SEQ ID NO.18), or 370–374 (SEQ ID NO.19) of human p53.

2. The peptide of claim 1, wherein at least one of said at least four amino acids is substituted by the corresponding residue from a non-human p53 sequence.

3. The peptide according to claim 1, wherein said at least four sequential amino acids are D-amino acids which map to the negative regulatory region represented by residues 361–383 of human p53 (SEQ ID NO. 2) in a reverse sequence orientation, relative to the wild-type sequence.

4. The peptide according to claim 1, wherein said peptide is cyclic.

5. A method of activating specific DNA binding activity of p53 comprising complexing said peptide of claim 1 with p53.

6. A peptidomimetic of a peptide which competes with an endogenous p53 negative regulatory region for binding with a negative regulatory region of p53, said peptidomimetic containing at least four sequential amino acids from a negative regulatory region which maps to residues 361–383 (SEQ ID NO.2) of p53, said peptide not being a subfragment of human p53, wherein said peptide activates, in a p53 DNA binding assay, DNA binding of wild-type p53 or a p53 mutant containing a single amino acid substitution, said mutant selected from the group consisting of p53-ser$^{239}$, p53-his$^{273}$, p53-gln$^{248}$, p53-trp$^{282}$, and p53-cys$^{273}$.

7. A peptidomimetic according to claim 6 wherein one or more peptide bonds are replaced by a reduced isostere pseudopeptide bond.

8. A peptidomimetic according to claim 6 wherein one or more peptide bonds are replaced by a retro-inverso pseudopeptide bond.

9. A peptidomimetic according to claim 6 wherein one or more amino acid residues are replaced by the corresponding N-substituted glycine.

10. A method of activating specific DNA binding activity of p53, comprising complexing
    (a) a peptide which competes with an endogenous p53 negative regulatory region for binding with a negative regulatory region of p53, said peptide containing at least four sequential amino acids from a negative regulatory region which maps to residues 361–383 (SEQ ID NO.2) of p53, said peptide not being a subfragment of human p53, wherein said peptide activates, in a p53 DNA binding assay, DNA binding of wild-type p53 or a p53 mutant containing a single amino acid substitution, said mutant selected from the group consisting of p53-ser$^{239}$, p53-his$^{273}$, p53-gln$^{248}$, p53-trp$^{282}$, and p53-cys$^{273}$, or
    (b) a peptidomimetic of said peptide with said wild-type p53 or with said p53 mutant.

11. A peptide which competes with an endogenous p53 negative regulatory region for binding with a negative regulatory region NRR1 comprising residues 361–383 of p53 or NRR2 comprising residues 300–321 of p53, said peptide containing at least four sequential amino acids from a negative regulatory region which maps to residues 361–383 of p53 (SEQ ID NO. 2), said peptide not being a subfragment of human p53, wherein said peptide activates, in a p53 DNA binding assay, DNA binding of wild-type p53 or a p53 mutant containing a single amino acid substitution, said mutant selected from the group consisting of p53-ser$^{239}$, p53-his$^{273}$, p53-gln$^{248}$, p53-trp$^{282}$, and p53-cys$^{273}$, and said peptide containing residues 363–373 (SEQ ID NO. 4), 368–380 (SEQ ID NO. 5), 373–383 (SEQ ID NO. 6), 371–383 (SEQ ID NO. 7), 363–382 (SEQ ID NO, 8), 367–386 (SEQ ID NO. 9), 363–386 (SEQ ID NO. 10), 362–386 (SEQ ID NO. 11), 360–386 (SEQ ID NO. 12), 363–370 (SEQ ID NO. 14), 368–373 (SEQ ID NO. 15), 368–372 (SEQ ID NO. 16), 369–373 (SEQ ID NO. 17), 370–375 (SEQ ID NO. 18), or 370–374 (SEQ ID NO. 19) of human p53.

12. A peptidomimetic of a peptide which competes with an endogenous p53 negative regulatory region for binding with a negative regulatory region NRR1 or NRR2 of p53, said peptidomimetic containing at least four sequential amino acids from a negative regulatory region which maps to residues 361–383 (SEQ ID NO. 2) of p53, said peptide not being a subfragment of human p53, wherein said peptide activates, in a p53 DNA binding assay, DNA binding of wild-type p53 or a p53 mutant containing a single amino acid substitution, said mutant selected from the group consisting of p53-ser$^{239}$, p53-his$^{273}$ p53-gln$^{248}$, p53-trp$^{282}$, and p53-cys$^{273}$.

13. A method of activating specific DNA binding activity of p53, comprising complexing
   (a) a peptide which competes with an endogenous p53 negative regulatory region for binding with a negative regulatory region NRR1 or NRR2 of p53, containing at least four sequential amino acids from a negative regulatory region which maps to residues 361–383 (SEQ ID NO. 2) of p53, said peptide not being a subfragment of human p53, wherein said peptide activates, in a p53 DNA binding assay, DNA binding of wild-type p53 or a p53 mutant containing a single amino acid substitution, said mutant selected from the group consisting of p53-ser$^{239}$, p53-his$^{273}$, p53-gln$^{248}$, p53-trp$^{282}$, and p53-cys$^{273}$, or
   (b) a peptidomimetic of said peptide with said wild-type p53 with said wild-type p53 or with said p53 mutant.

* * * * *

UNITED STATES PATENT AND TRADEMARK OFFICE
CERTIFICATE OF CORRECTION

PATENT NO. : 6,169,073 B1  Page 1 of 1
DATED : January 2, 2001
INVENTOR(S) : Thanos Halazonetis et al.

It is certified that error appears in the above-identified patent and that said Letters Patent is hereby corrected as shown below:

Title page,
Item [56], References Cited, OTHER PUBLICATIONS,
-- 41: -- has been inserted before "561-566 (1993)"; and
"Rgulation" has been replaced with -- Regulation --.
"Tanigaki et al, "The peptide binding specificityof HLA B27 subtypes",
Immunogenetics, vol. 40, pp. 192-198.*
Hupp et al. "Allosteric activation of latent p53 tetramers", Current Biology, vol. 4, No. 10, pp. 865-875.*
Powell et al, "Peptide stability in drug development. II. Effect of single amino acid substitution and glysosylation on peptide reactivity in human serum"
Parmaceutical Research, vol. 10, No. 9, pp. 1268-1273.*
Couder et al, "Synthesis and biological activities of hexapeptide of neutrotensin",
Int. J. Peptide Protein Res., vol. 41, pp. 181-184.*
Dalpozzo et al, "H-Gly-His(NHCO)Lys-OH, partially modifield retro-inverso analogue of the growth factor glycyl-L-histidyl-L-Lysine with enhanced enzymatic stability", Int. J. Peptide Protein Res., vol. 41, pp. 561-566*" have been removed from the granted patent.

Column 1,
Line 34, "ia" has been replaced with -- in a --; and
Line 38, "p53 trp$^{282}$, and p53 cys $^{273}$" have been replaced with -- p53-trp$^{282}$, and -- p53-cys$^{273}$ --.

Signed and Sealed this

Twenty-ninth Day of October, 2002

Attest:

JAMES E. ROGAN
Attesting Officer  Director of the United States Patent and Trademark Office

SEQUENCE LISTING (1) GENERAL INFORMATION:

(iii) NUMBER OF SEQUENCES: 35

(2) INFORMATION FOR SEQ ID NO: 1:

(i) SEQUENCE CHARACTERISTICS:
       (A) LENGTH: 1317 base pairs
       (B) TYPE: nucleic acid
       (C) STRANDEDNESS: double
       (D) TOPOLOGY: linear (ii) MOLECULE TYPE: cDNA (vi) ORIGINAL SOURCE:
       (A) ORGANISM: Homo sapiens (xi) SEQUENCE DESCRIPTION: SEQ ID NO: 1:

```
GTCTAGAGCC ACCGTCCAGG GAGCAGGTAG CTGCTGGGCT CCGGGGACAC TTTGCGTTCG     60
GGCTGGGAGC GTGCTTTCCA CGACGGTGAC ACGCTTCCCT GGATTGGCAG CCAGACTGCC    120
TTCCGGGTCA CTGCCATGGA GGAGCCGCAG TCAGATCCTA GCGTCGAGCC CCCTCTGAGT    180
CAGGAAACAT TTTCAGACCT ATGGAAACTA CTTCCTGAAA ACAACGTTCT GTCCCCCTTG    240
CCGTCCCAAG CAATGGATGA TTTGATGCTG TCCCCGGACG ATATTGAACA ATGGTTCACT    300
GAAGACCCAG GTCCAGATGA AGCTCCCAGA ATGCCAGAGG CTGCTCCCCC CGTGGCCCCT    360
GCACCAGCAG CTCCTACACC GGCGGCCCCT GCACCAGCCC CCTCCTGGCC CCTGTCATCT    420
TCTGTCCCTT CCCAGAAAAC CTACCAGGGC AGCTACGGTT TCCGTCTGGG CTTCTTGCAT    480
TCTGGGACAG CCAAGTCTGT GACTTGCACG TACTCCCCTG CCCTCAACAA GATGTTTTGC    540
CAACTGGCCA AGACCTGCCC TGTGCAGCTG TGGGTTGATT CCACACCCCC GCCCGGCACC    600
CGCGTCCGCG CCATGGCCAT CTACAAGCAG TCACAGCACA TGACGGAGGT TGTGAGGCGC    660
TGCCCCCACC ATGAGCGCTG CTCAGATAGC GATGGTCTGG CCCCTCCTCA GCATCTTATC    720
CGAGTGGAAG GAAATTTGCG TGTGGAGTAT TTGGATGACA GAAACACTTT TCGACATAGT    780
GTGGTGGTGC CCTATGAGCC GCCTGAGGTT GGCTCTGACT GTACCACCAT CCACTACAAC    840
TACATGTGTA ACAGTTCCTG CATGGGCGGC ATGAACCGGA GGCCCATCCT CACCATCATC    900
ACACTGGAAG ACTCCAGTGG TAATCTACTG GGACGGAACA GCTTTGAGGT GCGTGTTTGT    960
GCCTGTCCTG GGAGAGACCG GCGCACAGAG GAAGAGAATC TCCGCAAGAA AGGGGAGCCT   1020
CACCACGAGC TGCCCCCAGG GAGCACTAAG CGAGCACTGC CAACAACAC CAGCTCCTCT   1080
CCCCAGCCAA AGAAGAAACC ACTGGATGGA GAATATTTCA CCCTTCAGAT CCGTGGGCGT   1140
GAGCGCTTCG AGATGTTCCG AGAGCTGAAT GAGGCCTTGG AACTCAAGGA TGCCCAGGCT   1200
GGGAAGGAGC CAGGGGGGAG CAGGGCTCAC TCCAGCCACC TGAAGTCCAA AAAGGGTCAG   1260
TCTACCTCCC GCCATAAAAA ACTCATGTTC AAGACAGAAG GGCCTGACTC AGACTGA     1317
```

(2) INFORMATION FOR SEQ ID NO: 2:

(i) SEQUENCE CHARACTERISTICS:
       (A) LENGTH: 393 amino acids
       (B) TYPE: amino acid
       (C) STRANDEDNESS: unknown
       (D) TOPOLOGY: linear (ii) MOLECULE TYPE: protein (vi) ORIGINAL SOURCE:

(A) ORGANISM: Homo sapiens (xi) SEQUENCE DESCRIPTION: SEQ ID NO: 2:

```
Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
            85                  90                  95

Val Pro Ser Gln Lys Thr Tyr Gln Gly Ser Tyr Gly Phe Arg Leu Gly
        100                 105                 110

Phe Leu His Ser Gly Thr Ala Lys Ser Val Thr Cys Thr Tyr Ser Pro
    115                 120                 125

Ala Leu Asn Lys Met Phe Cys Gln Leu Ala Lys Thr Cys Pro Val Gln
130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
            165                 170                 175

Pro His His Glu Arg Cys Ser Asp Ser Asp Gly Leu Ala Pro Pro Gln
        180                 185                 190

His Leu Ile Arg Val Glu Gly Asn Leu Arg Val Glu Tyr Leu Asp Asp
    195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
        260                 265                 270

Arg Val Cys Ala Cys Pro Gly Arg Asp Arg Arg Thr Glu Glu Glu Asn
    275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
        340                 345                 350

Ala Gln Ala Gly Lys Glu Pro Gly Gly Ser Arg Ala His Ser Ser His
    355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390
```

(2) INFORMATION FOR SEQ ID NO: 3:

(i) SEQUENCE CHARACTERISTICS:
        (A) LENGTH: 390 amino acids
        (B) TYPE: amino acid
        (C) STRANDEDNESS: unknown
        (D) TOPOLOGY: linear (ii) MOLECULE TYPE: protein (vi) ORIGINAL SOURCE:
        (A) ORGANISM: Mus spretus (xi) SEQUENCE DESCRIPTION: SEQ ID NO: 3:

```
Met Thr Ala Met Glu Glu Ser Gln Ser Asp Ile Ser Leu Glu Leu Pro
1               5                   10                  15

Leu Ser Gln Glu Thr Phe Ser Gly Leu Trp Lys Leu Leu Pro Pro Glu
                20                  25                  30

Asp Ile Leu Pro Ser Pro His Cys Met Asp Leu Leu Leu Pro Gln
            35                  40                  45

Asp Val Glu Glu Phe Phe Glu Gly Pro Ser Glu Ala Leu Arg Val Ser
        50                  55                  60

Gly Ala Pro Ala Ala Gln Asp Pro Val Thr Glu Thr Pro Gly Pro Val
65                  70                  75                  80

Ala Pro Ala Pro Ala Thr Pro Trp Pro Leu Ser Ser Phe Val Pro Ser
                85                  90                  95

Gln Lys Thr Tyr Gln Gly Asn Tyr Gly Phe His Leu Gly Phe Leu Gln
                100                 105                 110

Ser Gly Thr Ala Lys Ser Val Met Cys Thr Tyr Ser Pro Pro Leu Asn
            115                 120                 125

Lys Leu Phe Cys Gln Leu Val Lys Thr Cys Pro Val Gln Leu Trp Val
130                 135                 140

Ser Ala Thr Pro Pro Ala Gly Ser Arg Val Arg Ala Met Ala Ile Tyr
145                 150                 155                 160

Lys Lys Ser Gln His Met Thr Glu Val Val Arg Arg Cys Pro His His
                165                 170                 175

Glu Arg Cys Ser Asp Gly Asp Gly Leu Ala Pro Pro Gln His Leu Ile
            180                 185                 190

Arg Val Glu Gly Asn Leu Tyr Pro Glu Tyr Leu Glu Asp Arg Gln Thr
        195                 200                 205

Phe Arg His Ser Val Val Val Pro Tyr Glu Pro Pro Glu Ala Gly Ser
210                 215                 220

Glu Tyr Thr Thr Ile His Tyr Lys Tyr Met Cys Asn Ser Ser Cys Met
225                 230                 235                 240

Gly Gly Met Asn Arg Arg Pro Ile Leu Thr Ile Ile Thr Leu Glu Asp
                245                 250                 255

Ser Ser Gly Asn Leu Leu Gly Arg Asp Ser Phe Glu Val Arg Val Cys
            260                 265                 270

Ala Cys Pro Gly Arg Asp Arg Arg Thr Glu Glu Glu Asn Phe Arg Lys
        275                 280                 285

Lys Glu Val Leu Cys Pro Glu Leu Pro Pro Gly Ser Ala Lys Arg Ala
    290                 295                 300

Leu Pro Thr Cys Thr Ser Ala Ser Pro Pro Gln Lys Lys Pro Leu
305                 310                 315                 320

Asp Gly Glu Tyr Phe Thr Leu Lys Ile Arg Gly Arg Lys Arg Phe Glu
                325                 330                 335
```

```
Met Phe Arg Glu Leu Asn Glu Ala Leu Glu Leu Lys Asp Ala His Ala
            340                 345                 350
Thr Glu Glu Ser Gly Asp Ser Arg Ala His Ser Ser Tyr Leu Lys Thr
            355                 360                 365
Lys Lys Gly Gln Ser Thr Ser Arg His Lys Lys Thr Met Val Lys Lys
            370                 375                 380
Val Gly Pro Asp Ser Asp
385                 390
```

(2) INFORMATION FOR SEQ ID NO: 4:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 4:

```
Arg Ala His Ser Ser His Leu Lys Ser Lys Lys
1               5                   10
```

(2) INFORMATION FOR SEQ ID NO: 5:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 5:

```
His Leu Lys Ser Lys Lys Gly Gln Ser Thr Ser Arg His
1               5                   10
```

(2) INFORMATION FOR SEQ ID NO: 6:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 6:

```
Lys Gly Gln Ser Thr Ser Arg His Lys Lys Leu
1               5                   10
```

(2) INFORMATION FOR SEQ ID NO: 7:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 7:

```
Ser Lys Lys Gly Gln Ser Thr Ser Arg His Lys Lys Leu
1               5                   10
```

(2) INFORMATION FOR SEQ ID NO: 8:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 8:

Arg Ala His Ser Ser His Leu Lys Ser Lys Lys Gly Gln Ser Thr Ser
1               5                   10                  15
Arg His Lys Lys
            20

(2) INFORMATION FOR SEQ ID NO: 9:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 9:

Ser His Leu Lys Ser Lys Lys Gly Gln Ser Thr Ser Arg His Lys Lys
1               5                   10                  15
Leu Met Phe Lys
            20

(2) INFORMATION FOR SEQ ID NO: 10:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO: 10:

Arg Ala His Ser Ser His Leu Lys Ser Lys Lys Gly Gln Ser Thr Ser
1               5                   10                  15
Arg His Lys Lys Leu Met Phe Lys
            20

(2) INFORMATION FOR SEQ ID NO: 11:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO: 11:

Ser Arg Ala His Ser Ser His Leu Lys Ser Lys Lys Gly Gln Ser Thr
1               5                   10                  15
Ser Arg His Lys Lys Leu Met Phe Lys
            20                  25

(2) INFORMATION FOR SEQ ID NO: 12:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 12:

Gly Gly Ser Arg Ala His Ser Ser His Leu Lys Ser Lys Lys Gly Gln
1               5                   10                  15

```
Ser Thr Ser Arg His Lys Lys Leu Met Phe Lys
            20                  25
```

(2) INFORMATION FOR SEQ ID NO: 13:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 13:

```
Lys Lys Ser Lys Leu His Ser Ser His Ala Arg
1               5                   10
```

(2) INFORMATION FOR SEQ ID NO: 14:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 14:

```
Arg Ala His Ser Ser His Leu Lys
1               5
```

(2) INFORMATION FOR SEQ ID NO: 15:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 15:

```
His Leu Lys Ser Lys Lys
1               5
```

(2) INFORMATION FOR SEQ ID NO: 16:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 16:

```
His Leu Lys Ser Lys
1               5
```

(2) INFORMATION FOR SEQ ID NO: 17:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 17:

```
Leu Lys Ser Lys Lys
1               5
```

(2) INFORMATION FOR SEQ ID NO: 18:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 18:

```
Lys Ser Lys Lys Gly Gln
1               5
```

(2) INFORMATION FOR SEQ ID NO: 19:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 19:

```
Lys Ser Lys Lys Gly
1               5
```

(2) INFORMATION FOR SEQ ID NO: 20:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 20:

```
Arg Ala His Ser His Leu Lys
1               5
```

(2) INFORMATION FOR SEQ ID NO: 21:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 21:

```
His Lys Ser Lys Lys
1               5
```

(2) INFORMATION FOR SEQ ID NO: 22:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO: 22:

```
Cys Gly Gly Ser Arg Ala His Ser His Leu Lys Ser Lys Lys Gly
1               5                   10                  15
Gln Ser Thr Ser Arg His Lys Lys Leu Met Phe Lys
                20                  25
```

(2) INFORMATION FOR SEQ ID NO: 23:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 23:

```
Cys Gly Ser Arg Ala His Ser Ser His Leu Lys Ser Lys Lys Gly Gln
1               5                   10                  15
Ser Thr Ser Arg His Lys Lys Leu Met Phe Lys
            20                  25
```

(2) INFORMATION FOR SEQ ID NO: 24:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO: 24:

```
Cys Gly Gly Ser Arg Ala His Ser Ser His Leu Lys Ser Lys Lys Gly
1               5                   10                  15
Gln Ser Thr Ser Arg His Lys Lys Leu Met Lys
            20                  25
```

(2) INFORMATION FOR SEQ ID NO: 25:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO: 25:

```
Cys Gly Ser Arg Ala His Ser Ser His Leu Lys Ser Lys Lys Gly Gln
1               5                   10                  15
Ser Thr Ser Arg His Lys Lys Leu Met Lys
            20                  25
```

(2) INFORMATION FOR SEQ ID NO: 26:

(i) SEQUENCE CHARACTERISTICS:
        (A) LENGTH: 1215 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 26:

```
GAATTCAACC AGCAGCCTCC CGCGACCATG GAGGAGCCGC AGTCAGATCC TAGCGTCGAG     60

CCCCCTCTGA GTCAGGAAAC ATTTTCAGAC CTATGGAAAC TACTTCCTGA AAACAACGTT    120

CTGTCCCCCT TGCCGTCCCA AGCAATGGAT GATTTGATGC TGTCCCCGGA CGATATTGAA    180

CAATGGTTCA CTGAAGACCC AGGTCCAGAT GAAGCTCCCA GAATGCCAGA GGCTGCTCCC    240

CCCGTGGCCC CTGCACCAGC AGCTCCTACA CCGGCCGCCC CTGCACCAGC CCCCTCCTGG    300
```

| | |
|---|---|
| CCCCTGTCAT CTTCTGTCCC TTCCCAGAAA ACCTACCAGG GCAGCTACGG TTTCCGTCTG | 360 |
| GGCTTCTTGC ATTCTGGGAC AGCCAAGTCT GTGACTTGCA CGTACTCCCC TGCCCTCAAC | 420 |
| AAGATGTTTT GCCAACTGGC GAAGACCTGC CCTGTGCAGC TGTGGGTTGA TTCCACACCC | 480 |
| CCGCCCGGCA CCCGCGTCCG CGCCATGGCC ATCTACAAGC AGTCACAGCA CATGACGGAG | 540 |
| GTTGTGAGGC GCTGCCCCCA CCATGAGCGC TGCTCAGATA GCGATGGTCT GGCCCCTCCT | 600 |
| CAGCATCTTA TCCGAGTGGA AGGAAATTTG CGTGTGGAGT ATTTGGATGA CAGAAACACT | 660 |
| TTTCGACATA GTGTGGTGGT ACCCTATGAG CCGCCTGAGG TTGGCTCTGA CTGTACCACC | 720 |
| ATCCACTACA ACTACATGTG TAACAGTTCC TGCATGGGCG GCATGAACCG GAGGCCCATC | 780 |
| CTCACCATCA TCACACTGGA AGACTCCAGT GGTAATCTAC TGGGACGGAA CAGCTTTGAG | 840 |
| GTGCGTGTTT GTGCCTGTCC TGGGAGAGAC CGGCGCACAG AGGAAGAGAA TCTCCGCAAG | 900 |
| AAAGGGGAGC CTCACCACGA GCTCCCCCCA GGGAGCACTA AGCGAGCACT GCCCAACAAC | 960 |
| ACCAGCTCCT CTCCCCAGCC AAAGAAGAAA CCACTGGATG GAGAATATTT CACCCTTCAG | 1020 |
| ATCCGCGGGC GTGAGCGCTT CGAAATGTTC CGAGAGCTGA ATGAGGCCTT GGAACTCAAG | 1080 |
| GATGCCCAGG CTGGGAAGGA GCCAGGGGGG AGCAGGGCTC ACTCCAGCCA CCTGAAGTCC | 1140 |
| AAAAAGGGTC AGTCTACCTC CCGCCATAAA AAACTCATGT TCAAGACAGA AGGGCCTGAC | 1200 |
| TCAGACTGAG TCGAC | 1215 |

(2) INFORMATION FOR SEQ ID NO: 27:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO: 27:

| | |
|---|---|
| GAGAGCCCCA GTTACCATAA CTACTCT | 27 |

(2) INFORMATION FOR SEQ ID NO: 28:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO: 28:

| | |
|---|---|
| ATCACGTGAT ATCACGTGAT ATCACGTGAT | 30 |

(2) INFORMATION FOR SEQ ID NO: 29:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO: 29:

CCCGAACATG TCCCAACATG TTGGGG                                              26

(2) INFORMATION FOR SEQ ID NO: 30:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO: 30:

TCGAGCATGT TCGAGCATGT TCGAGCATGT                                          30

(2) INFORMATION FOR SEQ ID NO: 31:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (xi) SEQUENCE DESCRIPTION: SEQ ID NO: 31:

CCGGGCATGT CCGGGCATGT CCGGGCATGT                                          30

(2) INFORMATION FOR SEQ ID NO: 32:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 32:

Lys Ser Lys Lys Gln
1               5

(2) INFORMATION FOR SEQ ID NO: 33:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 33:

Arg Ala His Ser Ser His Lys Lys
1               5

(2) INFORMATION FOR SEQ ID NO: 34:

(i) SEQUENCE CHARACTERISTICS:
        (A) LENGTH: 6 amino acids
        (B) TYPE: amino acid -continued

```
         (D) TOPOLOGY: linear (ii) MOLECULE TYPE: peptide (xi) SEQUENCE DESCRIPTION: SEQ ID NO: 34:

His Leu Lys Ser Arg His
1               5

(2) INFORMATION FOR SEQ ID NO: 35:

(i) SEQUENCE CHARACTERISTICS:
         (A) LENGTH: 20 base pairs
         (B) TYPE: nucleic acid
         (C) STRANDEDNESS: double
         (D) TOPOLOGY: linear (ii) MOLECULE TYPE: DNA (genomic)

(vi) ORIGINAL SOURCE:
         (A) ORGANISM: Homo sapiens (xi) SEQUENCE DESCRIPTION: SEQ ID NO: 35:

TGGCATGTCA TGGCATGTCA                                                  20
```